US011997959B2

(12) United States Patent
Zhang et al.

(10) Patent No.: US 11,997,959 B2
(45) Date of Patent: Jun. 4, 2024

(54) METHOD FOR BREEDING NEW VARIETY OF RATOON RICE CROP AND CULTIVATION METHOD FOR NEW VARIETY OF RATOON RICE CROP

(71) Applicant: GUANGXI JINGREN AGRICULTURAL SCIENCE AND TECHNOLOGY CO., LTD, Guangxi (CN)

(72) Inventors: Liyan Zhang, Guangxi (CN); Wuhan Zhang, Hunan (CN); Shunde Li, Hunan (CN); Hongyun Zhang, Hunan (CN)

(73) Assignee: GUANGXI JINGREN AGRICULTURAL SCIENCE AND TECHNOLOGY CO., LTD, Guangxi (CN)

( * ) Notice: Subject to any disclaimer, the term of this patent is extended or adjusted under 35 U.S.C. 154(b) by 279 days.

(21) Appl. No.: 17/296,057

(22) PCT Filed: Nov. 18, 2019

(86) PCT No.: PCT/CN2019/119082
§ 371 (c)(1),
(2) Date: May 21, 2021

(87) PCT Pub. No.: WO2020/108335
PCT Pub. Date: Jun. 4, 2020

(65) Prior Publication Data
US 2021/0392825 A1 Dec. 23, 2021

(30) Foreign Application Priority Data
Nov. 30, 2018 (CN) .......................... 201811455367.7

(51) Int. Cl.
A01G 22/22 (2018.01)
A01G 7/04 (2006.01)
A01H 6/46 (2018.01)

(52) U.S. Cl.
CPC ............ *A01G 22/22* (2018.02); *A01G 7/045* (2013.01); *A01H 6/4636* (2018.05)

(58) Field of Classification Search
None
See application file for complete search history.

(56) References Cited
U.S. PATENT DOCUMENTS
2014/0259905 A1   9/2014   Ovadya et al.

FOREIGN PATENT DOCUMENTS

| CN | 1094887 A | 11/1994 |
|---|---|---|
| CN | 1039770 C | 9/1998 |
| CN | 101176424 A | 5/2008 |
| CN | 104686268 A | 6/2015 |
| CN | 105188349 A | 12/2015 |
| CN | 108432579 A | 8/2018 |
| JP | H07-135861 A | 5/1995 |
| JP | 2005-176798 A | 7/2005 |
| JP | 5336332 B2 | 11/2013 |

OTHER PUBLICATIONS

Awan et al. Pak J. Bot. (1978) 10(2):209-213.*
Negalur et al. Int. J. Microbiol. App. Sci. (2017)6(5):1638-1653.*
Lin Wen-Xiong. Journal of integrative Agriculture (2019) 18(1): 246-247.*
Changfu, "Ratooning Rice Cultivation Technology", Beijing: Agriculture Press, May 31, 1993, 37 pages.
Hanlai, "Development of Photo-(Thermo)-Sensitive Genic Male Sterile Rice and Identification on Photo-Thermo-Responses Characters of Fertility Transformation", Hubei Agricultural Sciences Supplement, 1996, pp. 33-37.
International Search Report and Written Opinion for CPT International Patent Application No. PCT/CN2019/119082, dated Feb. 12, 2020.
Kanglin, "Ratooning Rice Can Also Produce High Yield", Yunnan Agricultural Science and Technology, Oct. 31, 1978, No. 5, pp. 27-29.
Minzong, "Primary Research on Short-Day Treatment and Stub-Retain Regeneration Of Late Rice And Early Rice", Journal of Guanxi Agricultural College, 1988, vol. 7, No. 2, pp. 7-13.
Shang et al., "Studies on the Critical Photoperiod for Panicle Initiation of Different Rice Cultivars", Journal of South China Agricultural College, Sep. 1980, vol. 1, No. 3, pp. 54-66.
International Rice Research Institute, "Rice Ratooning", 1988, 287 pages.
Junli et al., "Molecular Marker-Assisted Selection for Photocopied Sensitivity in Rice", Guangxi University, 2012.

* cited by examiner

Primary Examiner — Medina A Ibrahim
(74) Attorney, Agent, or Firm — Lathrop GPM LLP; James H. Velema, Esq.

(57) ABSTRACT

A method for breeding a new variety of a ratoon rice crop and a cultivation method for the new variety of a ratoon rice crop. The method comprises: breeding a photosensitive variety of a rice crop; growing a ratoon rice crop under conditions of a long photoperiod; and taking corresponding cultivation measures to extend the growth duration of the ratoon rice crop. The invention increases grain yield while also permitting more uniform maturity of a ratoon rice crop. When compared to existing methods for cultivating ratoon rice crops, the invention greatly improves the grain yield and quality of a ratoon rice crop, and has economic and social benefits.

8 Claims, 1 Drawing Sheet

METHOD FOR BREEDING NEW VARIETY OF RATOON RICE CROP AND CULTIVATION METHOD FOR NEW VARIETY OF RATOON RICE CROP

The present application claims priority to Chinese Patent Application No. 201811455367.7, entitled "METHOD FOR BREEDING NEW VARIETY OF RATOON RICE CROP AND CULTIVATION METHOD FOR NEW VARIETY OF RATOON RICE CROP", which is filed on Nov. 30, 2018, the entire contents of which are incorporated in this application by reference.

FIELD OF THE INVENTION

The invention relates to the field of plant breeding and cultivation, in particular to a ratoon rice breeding methods and cultivation methods thereof.

BACKGROUND OF THE INVENTION

Rice ratooning refers to the agricultural practice of utilizing the dormant buds survived on the stubble after harvesting main crop, which germinate ratoon shoots under suitable conditions of light, temperature, fertilizer and water, produce ratoon crop, and then mature to give a certain yield of rice. Rice ratooning has such unique advantages as no need for sowing, seedling breeding, transplanting and land preparation, which saves the costs of seeds, labor and fertilizer and reduces soil erosion, showing good economic and social benefits.

Ratoon rice has a long history of cultivation in China and has been planted since 1600 years ago. Before 1949, the distribution of ratoon rice in southern China was mostly sporadical. Ratoon rice was planted in small areas, or planted as a supplemental way for poor harvest in the main season, with very low yield. From 1950 to 1970, although there was a certain development of ratoon rice, due to the limitation of characteristics of varieties and cultivation techniques, the cultivated area was fluctuating, the yield was low, and concentrated production areas and a relatively stable rice field cultivation system may not be established. After the 1980s, with the advent of a batch of hybrid rice with high yield of main crop and strong regeneration capacity of ratoon, the formation of farming systems for hybrid middle-season rice and its ratoon rice, the deepening of research on cultivation techniques, and the importance attached by agricultural technology departments at all levels, there is a certain increase in the per unit area yield of ratoon rice, and rice ratooning has been developed rapidly in southern China.

However, there are still two main problems in the practice of rice ratooning. First, the yield of ratoon rice is still low, with the average yield between 150 kg/mu and 300 kg/mu in large fields. "Mu", China's traditional area unit, 1 mu is equivalent to 667 square meters. The whole growth period of ratoon rice is generally only 60 days to 80 days. A too short growth period makes it difficult to increase the biomass, which is a key bottleneck factor that restricts the improvement of per unit area yield of ratoon rice. Moreover, vegetative growth and reproductive growth happen simultaneously, leaving almost no separate vegetative phase, resulting in the biomass of one single panicle is too small. Secondly, the mature of the ratoon crop is not even, making it hard to choose the right harvest time, which has a certain impact on both the yield and the quality of rice. Therefore, further prolonging the growth period and improving the uniformity of mature time have become key issues in the research of rice ratooning.

SUMMARY OF THE INVENTION

In view of the above, the invention provides a method for variety selection of ratoon rice and a cultivation method of rice ratooning. The methods may prolong the growth period of ratoon crop, improve the mature uniformity, and thereby improving the yield per unit area and quality of ratoon rice.

In order to achieve the above object, the invention provides the following technical solutions.

The invention provides a method for cultivation of ratoon rice, wherein a photosensitive variety is selected and cultivated under long day conditions during the ratoon season; the photosensitive variety refers to a variety that long day may delay or prevent its photoperiod induction and thereby prolonging growth period; the long day refers to an illumination time per day longer than critical day length of the photosensitive variety.

The invention also provides a method of rice ratooning, comprising selecting a photosensitive variety and cultivating under long-day conditions during the ratoon season; the photosensitive variety refers to a variety that long day may delay or prevent its photoperiod induction and thereby prolonging the growth period; the long day refers to an illumination time per day longer than critical day length of the photosensitive variety.

In some specific embodiments of the invention, a photosensitive variety is selected and cultivated under continuous long-day conditions immediately after the completion of photoperiod induction of main crop. This measure may prevent or delay photoperiod induction of low-node ratoon buds, and make the low-node ratoon shoots more even. If the long-day treatment is not carried out until the ratoon season, a few low-node ratoon buds may have completed photoperiod induction, leading to early heading, but most of the ratoon buds and their tillers have not completed photoperiod induction yet, then the effect of long-day on rice yield and quality is limited.

In some specific embodiments of the invention, the main production is from ratoon shoots and their tillers derived from low-node buds, and germination and tillering from low-node buds may be promoted by means of variety selection and/or cultivation; the low-node buds are ratoon buds of the last 4th node and lower nodes.

In some specific embodiments of the invention, the duration of the long day in the ratoon season is for not less than 20 days.

In the present invention, a suitable photosensitive variety is selected as ratoon rice for cultivation, wherein the key period of the long-day treatment is in the ratoon season, with a treatment time lasts for not less than 20 days. If the long-day treatment time is less than 20 days, the growth time for the low-node shoots and their tillers may not be enough, meanwhile, the vegetative growth is insufficient. Although the yield may be increased as compared with the conventional ratoon rice, the increase of yield is still limited. If the long-day treatment is 20 days or more than 20 days, the low-node shoots and their tillers will have a longer vegetative phase with high biomass and high yield, and the increase of yield of rice was higher than that of conventional ratoon rice.

In some specific embodiments of the invention, the long day begins immediately after the harvest of main crop or at any time after the harvest of main crop.

In some specific embodiments of the invention, the long-day conditions are provided by way of natural illumination or artificial illumination, the artificial illumination may be switched to natural illumination, or the artificial illumination interrupts the continuous dark cycle; the length and/or intensity of the long illumination may prevent or delay photoperiod induction of ratoon shoots and tillers thereof.

In some specific embodiments of the invention, the long-day conditions are provided by natural illumination or artificial illumination. Preferably, the artificial illumination is provided by ways as follows:

immediately after dark, providing illumination at an illuminance of not less than 1000 Lx, which is greater than the critical day length of the variety when added together with the natural day length; and/or in a continuous dark cycle, illumination is provided at an illuminance of not less than 1000 Lx for no shorter than 30 minutes.

The above illumination length and illuminance per day may ensure that photoperiod induction of almost all varieties is prevented or delayed. Considering the differences among varieties, the illuminance of some varieties may be lower than 1000 Lx, and the time required to break the continuous dark cycle may be shorter than 30 min, thus the illuminance of supplemental illumination may be reduced and the supplemental illumination time may be shorten so as to be more economical and environmentally friendly.

In some specific embodiments of the invention, the photosensitive variety is a low-node ratoon variety and suitable to low stubble treatment; and the low-node ratoon variety refers to a variety that the low-node ratoon buds account for more than 30% of ratoon buds from all-nodes (self-define, the same below) in the case of high stubble treatment, and the low stubble treatment refers to retaining low-node buds only, with the stubble height of 8-15 cm.

In some specific embodiments of the invention, wherein the accumulative fertilization amount already applied in the ratoon season accounts for 70% to 90% of the total fertilization amount in the whole growth period of the ratoon season till the treatment under long-day conditions has been completed. In some specific embodiments of the invention, the water management of the low stubble treatment is specifically as: maintaining a no-water layer or a thin-water layer with a water depth of no more than 3 cm for 7 days after the harvest of main crop under the premise that the water content of soil is greater than 60%.

In some specific embodiments of the invention, the long day begins immediately after photoperiod induction of main crop is completed. Completion of the photoperiod induction of main crop is not a necessary condition of the invention, but is beneficial to prevent or delay photoperiod induction of low-node ratoon buds. During the photoperiod induction process of main crop, a few ratoon buds complete photoperiod induction. If the long day is given immediately after the completion of photoperiod induction of main crop, the low-node ratoon buds basically have not complete photoperiod induction at that time, and the long day may prevent or delay photoperiod induction of the low-node ratoon buds, further improving the uniformity of the mature rice as well as the yield.

In some specific embodiments of the invention, the long-day treatment begins immediately after the harvest of main crop or after a period of time after the harvest of main crop. There is no doubt that the long-day treatment begins immediately after the harvest of main crop may prevent or delay photoperiod induction of a portion of ratoon shoots germinated from low-node ratoon buds and all their tillers. However, if cultivation is carried out in short-day conditions firstly after harvesting for a while and then under long-day conditions, the situation will be different. Taking Sanya, Hainan as an example, suppose that the critical day length of a variety is equivalent to the natural day length of May 22, then the natural day length from May 23 to July 21 in Sanya, Hainan will be the long day for this variety. However, for certain reasons, main crop must be harvested on April 22, then the ratoon season from April 22 to May 22 will be under the short-day conditions of the variety. In this period, most of the grown-up ratoon shoots have basically completed photoperiod induction, and this process is no irreversible since photoperiod induction has been completed. At this point, even under long-day conditions, the effect of prolonging the growth period is little. Therefore, it is necessary to consider it according to the situation:

if the number of the ratoon shoots is ≤⅓ of the maximum number of expected shoots, then an enhanced management of water and fertilizer is needed;

if the number of the ratoon shoots is >⅓ of the maximum number of expected shoots, then the growing points of young panicles are cut off and/or the stubble is retained for 5 to 10 cm.

Rice has the characteristic of automatic regulation. If the number of shoots is already enough, the tillering will automatically slow down or even stop. After the harvest of main crop, if the stubble is placed under short-day conditions firstly for a period then subjected to the long-day treatment, then from the harvest of main crop to the long-day treatment, a routine process for rice ratooning is going on, and almost all the ratoon shoots have completed photoperiod induction. If there are too many tillers and the number of ratoon shoots is >⅓ of the maximum number of expected shoots, the ratoon shoots will no longer tiller or tiller less even if given long day. Long day may not prolong the growth period of the original ratoon shoots, or the impact from long day is little. Therefore, at this time, the growing points of young panicle of the ratoon shoots may be cut off and/or the stubble may be kept for 5 to 10 cm. If there are not many tillers and the number of ratoon shoots is ≤⅓ of the maximum number of expected shoots, the ratoon shoots will continue to tiller under long-day conditions. These tillers generally have not completed photoperiod induction, and the growth period may be significantly prolonged. Moreover, the vegetative growth of these tillers is vigorously, whereas the original small amount of ratoon shoots has already completed heading and grain formation with little effect on total yield.

There is another case where, if there is a plenty of time or the first ratoon crop ripens earlier, a successive routine rice rationing may be carried out and harvested. For the successive rice rationing, preferably, a low stubble treatment, the cultivation method and the long-day treatment are the same as the rice rationing directly after the harvest of main crop.

When selecting a photosensitive variety for rice ratooning, the photosensitive variety with a suitable critical day length is a key for the application of the invention. The annual variation of day length for the Earth's northern and southern hemispheres is basically the same, but there are differences in the time. For example, the northern hemisphere has the longest day length around June 21, at that time the day length of the southern hemisphere is the shortest; the southern hemisphere has the longest day length around December 22, at that time the day length of the northern hemisphere is the shortest. Therefore, the method for determining the critical day length is described here by taking the equatorial region and the tropics and the subtropics of the northern hemisphere as examples. A method for determining the critical day length in the southern hemisphere may be apparent for those skilled in the art.

In the equatorial region, rice may be planted year round and the day length is almost unchanged throughout the year. The critical day length of a photosensitive variety is equal to or shorter or longer than the natural day length. If the critical day length is longer than or equal to the natural day length, then the natural illumination cannot prevent or delay photoperiod induction, so the photoperiod induction of ratoon shoots and their tillers in the ratoon season can only be prevented or delayed by supplemental illumination. Due to the suitable light and temperature conditions, after the harvest of first ratoon rice, supplemental illumination may be used for the photoperiod induction of successive ratoon buds in next season. If the critical day length is shorter than the natural day length, it is difficult to complete photoperiod induction under natural illumination conditions or it will take too much time. Artificial shading treatment is required to complete photoperiod induction. After the harvest of main crop under the shading treatment, shading treatment is also required to complete photoperiod induction in successive ratoon season, and the same for following seasons. In both cases, one-time sowing and multiple ratoon and harvest can be achieved. The variation of day length in the vicinity of the equatorial region is small, and the method for determining the critical day length of a photosensitive variety may also be referred to that for the equatorial region.

Rice may be planted year round in the tropics where the variations in the day length are huge. For example, in Sanya, Hainan, China, the longest natural day length of June 21 and the shortest day length of December 22 are quite different. A photosensitive variety with a critical day length between the two may be selected. The photoperiod induction of the main crop is completed under the short day, and the growth period of the ratoon crop is prolonged under the long day, and then photoperiod induction of the ratoon shoots and their tillers is completed when the long day switches to short day. Taking Sanya as an example, all the photosensitive varieties whose critical day length is not shorter than the natural day length of March 21 and not longer than that of June 12 can achieve the invention. As for a photosensitive variety with a critical day length comparable to the natural day length of March 21, all the natural day lengths from March 22 to July 22 are longer than the critical day length of the variety. It may be arranged to complete photoperiod induction before March 21, and to harvest the main crop around May 22, and to perform the long-day treatment on ratoon crop within 2 months of May 22 to July 22, providing a sufficient vegetative phase. Heading begins on August 22, and ratoon rice is harvested at the end of September. As for a photosensitive variety with a critical day length comparable to the natural day length of June 12, the main crop is harvested on June 12, and the long-day treatment of about 20 days from June 13 to July 2 for rice ratooning is performed. The invention requires the long-day treatment for not less than 20 days in the ratoon season, which is the minimum requirement for the treatment. Therefore, in Sanya, all the photosensitive varieties with a critical day length not less than the natural day length of March 21 and not longer than that of June 12 may be used to realize the invention by use of the natural illumination, and may be flexibly selected according to requirements. Certainly, in the tropics where rice may be planted year round, the technical solutions of supplemental illumination and shading in the equatorial area can also be used for reference to realize one-time sowing and multiple rationing and harvesting of rice. A combination treatment of natural long day, short day plus artificial illumination and shading can also be used in this region.

In subtropics, such as Nanning (Guangxi Province), Changsha (Hunan Province), etc., rice may not be planted in winter and double cropping rice is in practice, the day length for such regions varies greatly. The distinguishing feature of these regions is that it is constrained by the conditions of light and temperature. Early rice (crop) in the region is generally harvested in July, and the general photosensitive varieties are harvested by the end of July or mid-August. However, the longest day in the northern hemisphere is about June 21. For a photosensitive variety with a long critical day length, the natural day length is shorter than the critical day length after the harvest. For a photosensitive variety with a short critical day length, photoperiod induction often cannot be completed in the first half of the year, so it only grows one season in a year. This problem may be solved by the following methods: selecting a variety with a short basic vegetative phase, or using the greenhouse or low-latitude area for off-site seedling in advance, or selecting a variety resistant to low temperature during seedling stage to plant in advance. The above methods may also be combined. Due to the limitation of light and temperature conditions, the selection range of the critical day length of the photosensitive varieties in this region is also narrow. Taking Nanning as an example, in order to ensure high yield, main crop harvest is better not earlier than June 30, if 20 days of the shortest natural long day treatment is considered, the critical day length of the photosensitive variety may not be longer than the natural day length of July 20. Raising seedlings may be carried out at low latitudes or by covering films for warming, but it is unrealistic to cover films for warming in large fields. The earliest time for raising seedlings is the beginning of February in low latitudes or in the greenhouse, and transplant is carried out at the end of February. Due to the low temperature in March and April, it is relatively early to complete main crop photoperiod induction before April 20. Therefore, the critical day length of a photosensitive variety should not be shorter than the natural day length of April 20. Therefore, for a photosensitive variety to be used according to the invention in Nanning area, the critical day length of which is not shorter than the natural day length of April 20 and not longer than that of July 20. Certainly, if illumination shading and supplemental illumination are used, more combinations may be used.

The above description only describes the basic principles for selecting a photosensitive variety with a certain critical day length. Some general conditions are discussed, and for some special conditions, differences may exist. The natural day length data mentioned in the invention is replaced by meteorological observation data of day length (the time of a day from sunrise to sunset), and there may be slight but small differences with the actual natural day length and the data has very good reference value, and specifically the test results shall prevail. The invention will be further illustrated in conjunction with examples.

In some specific embodiments of the invention, when main crop is harvested, it is preferred to retain ratoon buds of the last 4th node and lower nodes, with a stubble height of 8-15 cm.

The yield of ratoon rice of the invention mainly comes from low-node ratoon shoots and their tillers. In the long-day treatment, most of the low-node ratoon shoots and all their tillers have not completed photoperiod induction yet, thus the long day which is longer than its critical day length may prevent or delay photoperiod induction, thus prolonging its growth period. Therefore, a low-node ratoon variety is preferred, the low-node buds refer to ratoon buds of the last 4th node and below, and the low-node ratoon variety refers to a variety that the low-node ratoon buds account for more than 30% of ratoon buds from all-nodes in the case of the high stubble treatment. In the case of the high stubble treatment, generally high-node ratoon buds will germinate first with a high germination rate and complete photoperiod induction early, which has greatly difference with low-node buds in mature time, and does not contribute much to the yield of ratoon rice of the present invention. However, both the ratoon shoots from the high-node ratoon buds and long stubble of main crop will have an adverse effect on the germination and tillering of the low-node ratoon buds. Therefore, it is preferable to leave a low stubble. The general height of the last 4 nodes of stubble is about 8 cm, and the general height of the last 3 nodes is about 15 cm. Therefore, the stubble height of 8~15 cm is suitable. In the production practice, ratoon shoots are generally germinated from the base of the stubble after the operation of harvester, and the method may be borrowed and improved.

In some specific embodiments of the invention, the low-node ratoon variety is selected from hybrid varieties from the hybridization between japonica or indica and japonica and wild rice.

In some specific embodiments of the invention, under the conditions of the natural illumination, in order to ensure that main crop is harvested on time, and ratoon crop is cultivated under natural long-day conditions, a photosensitive variety with short basic vegetative phase and/or low temperature tolerance at seedling stage are screened or bred, and/or the planting methods of early sowing, early seedling raising in the greenhouse and low-latitude off-site seedling raising are adopted.

The water and fertilizer management indicated in the invention is related to soil fertility, target yield, and fertilization habit. The principles of fertilization are: the long-day treatment period is equivalent to the tillering period of main crop, and the growth of crop is quite strong. The fertilization amount already applied in the ratoon season accounts for 70% to 90% of the total fertilization amount in the whole growth period of the ratoon season accumulatively till the treatment under long-day conditions has been completed. The post-management of ratoon rice in the invention is comparable to the management of the local rice planting at the same time, including drying paddy field, fertilizer and water management, and pest control, etc. The fertilization methods, such as applying more when the soil is fertile, applying less when the soil is barren, topdressing depending on seedlings, which are well-known to those skilled in the art, are all within the protection scope of the invention. The specific data given in the specific embodiments of the invention cannot be used as the limitation for the protection scope of the invention.

When short stubble is left, the soil of main crop is kept moist for 7 days after harvesting. It is preferred to maintain a no-water layer or a thin-water layer with a water depth of not more than 3 cm when the soil water content is greater than 60%. Deep water storage is not conducive to the germination and growth of low-node ratoon buds. Water flooding may directly cause the death of ratoon buds, resulting in serious vacancy plants.

In some specific embodiments of the invention, the test site is Nanning, Guangxi. Nanning is located on the south side of the Tropic of Cancer with a humid subtropical monsoon climate. The annual average temperature is about 21.6 degrees, the extreme maximum temperature is 40.4 degrees, and the extreme minimum temperature is −2.4 degrees. The light and temperature resources are abundant. A significant difference between Nanning and the tropics such as the equatorial region and Sanya is that rice cannot be planted on an annual basis.

Early rice in Nanning is usually planted at the end of February and harvested at the beginning of July, whereas the longest day in the year appears around June 21. Due to the limitation of early light and temperature conditions, main crop is generally arranged to be harvested at the end of June and early July. Early harvest is easy to lead to an insufficient growth period and a low yield of main crop. Ratoon rice shall be treated with the long-day treatment for not less than 20 days using the technology of the invention. Performing calculation according to harvesting main crop on June 30. After 20 days (July 20), the natural day length is 13 hours and 12 minutes, thus the critical day length of the selected photosensitive variety should be shorter than 13 hours and 12 minutes. Considering that in early February, artificial greenhouses or low-latitude areas (such as Hainan) may be used for seedling breeding in advance, and seedling transplanting may be carried out in late February and early March, the temperature in the early stage is low, thus it is relatively early to complete photoperiod induction before April 20. Therefore, the critical day length of the selected photosensitive variety must be longer than 12 hours and 47 minutes (the natural day length of April 20). Therefore, with the condition that the invention is realized by natural illumination, the critical day length of the photosensitive variety selected in Nanning area is preferable to be 12 hours and 47 minutes to 13 hours and 12 minutes. At the same time, it is necessary to ensure that main crop is harvested at the end of June and early July.

A variety with a critical day length of about 13 hours and 10 minutes may be selected by screening or breeding, considering that the natural day length in Nanning area from May 12 to July 31 will be greater than the critical day length of the variety. An appropriate growth period plus a reasonable sowing schedule makes the variety complete spike primordium differentiation before May 12 and main crop be harvested before June 30. After the harvest of main crop, the key technologies provided by the invention are used, such as leaving the low stubble, remaining a no-water layer or a thin-water layer with the water depth of not more than 3 cm within 7 days after the harvest of main crop under the premise that the water content of soil is greater than 60%. The fertilization amount already applied in the ratoon season accounts for 70% to 90% of the total fertilization amount in the whole growth period of the ratoon season accumulatively till the treatment under long-day conditions has been completed. Early fertilization and heavy fertilization will promote the ratoon shoots to produce a large number of tillers. After August 1, it will be transferred to the stage of spike primordium differentiation, heading Begins in early September, and ratoon rice is harvested in the early and mid-October. If it is necessary to further prolong the growth period of ratoon rice, it may be achieved by sowing in advance or breeding of similar photosensitive varieties with shorter growth period. However, due to the limitations of temperature and light conditions, the adjustable range is relatively small.

The subtropics such as Nanning and Changsha are quite rich in light and temperature resources, but rice still cannot be planted on an annual basis. The natural illumination may be used to achieve sowing for one season and harvesting for two seasons. It can also refer to the situation in the equatorial region. By means of illumination shading and supplemental illumination, it is possible to select photosensitive varieties with suitable critical day lengths. If a variety with strong photosensitivity is selected and the photoperiod induction of main crop is interrupted by illumination shading treatment, ratoon rice will make full use of the light and temperature resources in the second half of the year; if ratoon rice is under natural illumination conditions shorter than its critical day length, its reproductive phase may also be prolonged by supplemental illumination. The implementation of the invention will be more flexible by means of artificial illumination shading and supplemental illumination. These contents will be apparent to those skilled in the art and will not be described again.

In the above experimental protocol, the photosensitive variety is Lingliangyou 472, the National Authorized Rice 2010001, which is used as the double cropping late rice in South China. For the main crop, sowing date: February 1; location: Wanning, Hainan; transplanting date: February 26; heading beginning date: May 20; ripening date: June 26. The whole growth period: 146 days. For ratoon season (low stubble treatment), heading beginning date: August 28; ripening date: October 12. The whole growth period: 108 days.

The critical day length of Lingliangyou 472 is about 13 hours and 10 minutes. Day length of Nanning from May 11 to August 1 is greater than the critical day length of Lingliangyou 472. Under the premise of using only the natural illumination and no illumination shading, main crop of Lingliangyou 472 must complete photoperiod induction before May 11. In order to be able to be treated for more than 30 days under long-day conditions during the ratoon season, main crop needed to be harvested before June 30. In 2018, seedling cultivation was carried out Wanning, Hainan on February 1, and transplanted to the experimental field in Nanning on February 26.

Preferably, in the above test, there are 30 holes per square meter with 2 grains of rice seedlings per hole. Enough base fertilizer was applied, top dressing was applied early, and nitrogen was strictly controlled in the late stage. The test field was medium-fertilized soil, applying 40 kg of 25% rice special compound fertilizer per mu ("mu", Chinese traditional area unit, equivalent to 667 square meters) as the base fertilizer, and applying together with herbicide 7 days after transplanting, applying 7.5 kg of urea per mu additionally, and applying 7 kg potassium chloride per mu at early spike primordium differentiation stage. During the tillering stage, the dry and the wet conditions raised alternately to promote tillering. When the total number of seedlings per mu reached 250,000 seedlings, water releasing and paddy field drying were performed in time. The booting stage was dominated mainly by wetting, and a shallow water layer was maintained during the heading stage. The grouting stage was dominated by moistening, and it was forbidden to drain off water too early. Pay attention to the timely prevention and control of pests and diseases, such as rice blast, bacterial leaf blight, striped rice borer, rice leaf roller, sheath blight and rice planthopper, etc., and it was harvested when about 90% of the grains were matured, maintaining the ratoon rice stubble healthy and ratoon buds strong. Leave a low stubble and keep the soil moist but no water layer can be seen within 10 days after the harvest of main crop. On the 11th day, shallow water was applied, and 25% of rice special compound fertilizer and 7.5 kg of urea were applied per mu. In the late stage, the dry and the wet conditions arised alternately to promote tillering, and when the total number of seedlings per mu reached 250,000 shoots, water releasing was performed in time. At the beginning of August, 5 kg of potassium chloride per mu was applied at early spike primordium differentiation stage. The whole growth period of the ratoon season lasted for 108 days.

In the above experiments, the yield of ratoon rice of the invention is significantly higher than that of the double cropping late rice, and the growth period of the double cropping late rice is longer than that of ratoon rice, and the two seem contradictory. In fact, that is not the case. For the ratoon crop, the stubble has a certain nutrient storage, generally from which 3 to 5 sturdy ratoon buds may be directly germinated within 3 to 8 days. Whereas for the double cropping late rice having 3 to 5 basic seedlings, it takes 20 to 30 days from sowing to planting to field, and 5 to 7 days for seedling readaption after planting. Therefore, ratoon rice may save 20 to 30 days as compared to the double cropping late rice. Lingliangyou 472 has a ratoon season for 108 days which is equivalent to 128-138 days for double cropping late rice, which ensure a sufficient vegetative phase. Under suitable conditions such as fertilizer, water, light and temperature, it has a high yield potential.

In other specific embodiments of the invention, Nanning was selected to simulate the equatorial region for testing. Specific practices were as follows: the rice variety RH with strong photosensitivity was selected, and the natural day length in the equatorial region was longer than the critical day length of RH. The natural day length of Nanning from February 18 to October 23 was longer than the critical day length of RH. Test for ratoon rice cultivation could be performed using a strongly photosensitive rice variety in Nanning where the equatorial region may be simulated. RH is a variety has strong photosensitivity from Southeast Asia with poor agronomic traits. This experiment only verifies that the invention can prolong the growth period of ratoon rice and improve its mature uniformity, without considering yield and other traits. Prolonging the growth period and improving the mature uniformity are the basis for realizing the high yield and high quality of ratoon rice. Those skilled in the art may refer to the present embodiment, select a newly developed variety with strong photosensitivity, and learn from the key technologies of the invention to realize one-time sowing and multiple harvesting, with high yield and efficiency.

In the above trial protocol in Nanning, sowing was on February 26 and transplantation was on April 3. From May 10, black and white films were used for illumination shading treatment, with the white side facing up and the black side facing down. Only 9 hours of natural illumination was given per day for 30 consecutive days. For medium-fertilized soil, applying 40 kg of 25% rice special compound fertilizer per mu as the base fertilizer, and applying together with herbicide 7 days after transplanting, applying 7.5 kg of urea per mu additionally, and applying 7 kg potassium chloride per mu at early spike primordium differentiation stage on May 20. Heading Beginning was on June 12 and harvesting was on July 15. The stubble was left low (about 12 cm). The soil was kept moist but no water layer could be seen within 7 days after harvesting, and the drainage work was done in rainy weather. On the 11th day, shallow water was applied, and 25% of rice special compound fertilizer and 7.5 kg of urea were applied per mu. In the late stage, the dry and the wet conditions were used alternately to promote tillering, and when the total number of seedlings per mu reached 200,000 seedlings on August 15, water, releasing, paddy field drying and seedlings control were performed. On August 25, black and white films were used for illumination shading treatment, with the white side facing up and the black side facing down. Only 9 hours of natural illumination was given per day for 30 consecutive days. At early spike primordium differentiation stage on September 5, 5 kg of potassium chloride per mu was applied. Heading Beginning was on October 3 and harvesting was on November 20. The whole growth period of the ratoon season lasted for 127 days.

The above trial protocol not only simulated the shaded annual planting in the tropics, but also had a guiding significance for local Nanning and similar areas. It takes time for the earth to heat up and cool down. Assume the longest day length of June 21 as a midpoint. The time suitable for rice growth in the early period is short (from the end of February to June 21, about 4 months), and the time suitable for rice growth in the late stage is long (from June 21 to November 20, about 5 months). In order to make full use of the light and temperature conditions, a strongly photosensitive variety with a shorter critical day length (but longer than the critical day length of RH and no need for illumination shading during the ratoon season) may be selected. The example is optional a variety whose critical day length is the same as the natural day length of August 20. According to the change regularity of natural day length, the natural day length from April 20 to August 20 is longer than the critical day length of the variety. The general variety would be difficult to complete photoperiod induction before April 20 if it was planted at the end of February. Therefore, photoperiod induction of main crop may be completed by the illumination shading treatment after April 20. After August 20, the natural day length was less than the critical day length, and ratoon rice may successfully complete photoperiod induction without the need for artificial illumination shading. Full heading was at the end of September and harvesting was in mid-November, thus it may make good use of the annual light and temperature resources.

In other specific embodiments of the invention, a simulated supplemental illumination trial was performed. Test variety: Lingliangyou 472. Treatment time: August 1 to August 30, the natural day length at this time is shorter than the critical day length of Lingliangyou 472. Treatment 1: illumination with an illuminance of 1000 Lx was added at the stump of rice for 1 hour per day when it was getting dark; treatment 2: illumination with an illuminance of 1000 Lx was added at the stump of rice at 23:30-24:00 for 30 minutes per day; and treatment 3: no illumination. This example was only for verifying the effect of supplemental illumination to prolong the growth period and improve the uniformity when matured, and the production was not measured. In the above embodiment, main crop was sown on February 26, transplanted on April 3, and harvested on July 31. The stubble was left low (about 12 cm). The illumination-supplied ratoon rice began seedling heading around September 28, in this course only a very small amount (<5%) of ratoon shoots regenerated ears early, and the uniformity was good when matured. The illumination-unsupplied ratoon rice (conventional ratoon rice) began seedling heading on August 28, and the uniformity when matured is poor.

In other specific embodiments of the invention, the invention is implemented in the equatorial region, where the light and temperature resources are abundant, and the day length is relatively stable, with the annual day length between 12 hours and 6 minutes and 12 hours and 7 minutes. The varieties with a critical day length of 12 hours and 6 minutes or less may be selected by screening or breeding, such as those with similar photosensitivity to RH, and the critical day length of RH is about 11 hours and 28 minutes. Photoperiod induction may be interrupted by illumination shading treatment, with shading for 8 to 30 days, and giving 9-10 hours of natural illumination every day. When photoperiod induction is completed or the spike primordiums are differentiated to phase 2, it may be transferred to natural illumination. After 20 days of harvesting main crop, the key techniques provided by the invention is used, such as illumination shading for 8 to 30 days, with giving 9 to 10 hours of natural illumination per day. A low stubble is left, and a no-water layer or a thin-water layer with the water depth of not more than 3 cm is remained within 7 days after the harvest of main crop under the premise that the water content of soil is greater than 60%. The fertilization amount already applied in the ratoon season accounts for 70% to 90% of the total fertilization amount in the whole growth period of the ratoon season accumulatively till the treatment under long-day conditions has been completed. Early fertilization and heavy fertilization will promote the ratoon shoots to produce a large number of tillers. 30 days after the harvest, main crop may be treated with illumination shading again according to the specific situation, so that it can enter the reproductive growth stage smoothly. After the harvest of ratoon rice, the above treatment may be repeated to achieve the purpose of one-time sowing and multi-year harvesting. Also a photosensitive variety with a critical day length of longer than 12 hours and 7 minutes may be selected. After the harvest of main crop, the key technologies provided by the invention, such as supplemental illumination for more than 20 days, may be utilized, and the time for the long-day treatment may be flexibly determined as needed. A low stubble is left, and a no-water layer or a thin-water layer with the water depth of not more than 3 cm is remained within 7 days after the harvest of main crop under the premise that the water content of soil is greater than 60%. The fertilization amount already applied in the ratoon season accounts for 70% to 90% of the total fertilization amount in the whole growth period of the ratoon season accumulatively till the treatment under long-day conditions has been completed. Early fertilization and heavy fertilization will promote the ratoon shoots to produce a large number of tillers. After the harvest of ratoon rice, the above treatment may be repeated to achieve the purpose of one-time sowing and multi-year harvesting.

In other specific embodiments of the invention, the experimental site is Sanya, Hainan. Sanya is located at a low latitude and is a tropical maritime monsoon climate zone with abundant light and temperature resources. The annual average temperature is 25.7° C., and the month with the lowest temperature is January with an average temperature of 21.4° C. It is known as the "natural greenhouse". The longest day length is 13 hours and 13 minutes on June 21; and the shortest day length is 11 hours and 2 minutes on December 22. The annual sunshine time is 2534 hours. The temperature and light conditions in Sanya are good, rice may be planted on an annual basis, and the sowing time is relatively free. In theory, without considering other factors, if the time of at least 20 days is longer than the critical day length of a photosensitive variety in Sanya, that is, the critical day length of which is not longer than 13 hours and 10 minutes (June 6 to July 6), then the invention may be applied to the variety. The growth period of ratoon rice is not the longer the better. If the growth period lasts for too long, on the one hand, the economic benefits will decline, and on the other hand, the cornice arrangement of main crop and other crops will be affected. In the exclusion of certain special circumstances, it will generally gat better economic benefits to give a long-day treatment within 2 months. In addition, the late-period booting and grouting of main crop may be cultivated under long-day conditions, generally in about 2 months, and the total time exceeding the critical day length of the photosensitive variety is preferably not more than 4 months. The critical day length should be not shorter than 12 hours and 40 minutes (April 22 to August 22). Therefore, if natural illumination conditions are used, a photosensitive variety with a critical day length between 12 hours and 40 minutes and 13 hours and 10 minutes should be used in Sanya.

Taking a variety whose critical day length is 12 hours and 47 minutes as an example. Day length of the Sanya area from May 1 to August 11 is longer than the critical day length of the variety. According to the growth period and reasonable sowing schedule, the spike primordium differentiation of the variety should be completed before May 1 and main crop will be harvested around June 20. After the harvest of main crop, the key technologies provided by the invention were utilized, such as leaving a low stubble, remaining a no-water layer or a thin-water layer with the water depth of not more than 3 cm within 7 days after the harvest of main crop under the premise that the water content of soil is greater than 60%. The fertilization amount already applied in the ratoon season accounts for 70% to 90% of the total fertilization amount in the whole growth period of the ratoon season accumulatively till the treatment under long-day conditions has been completed. Early fertilization and heavy fertilization will promote the ratoon shoots to produce a large number of tillers. After August 11, it was transferred to the stage of spike primordium differentiation, heading beginning was in early September, and the harvest was in mid-October. If it is necessary to further prolong the growth period of the rice ratoon season, it may be achieved by early sowing or breeding of similar photosensitive varieties with short growth period. After the harvest of ratoon rice, since the natural day length is shorter than the critical day length of the photosensitive variety, it may be resown in the coming year. It may also refer to the supplemental illumination measures in the equatorial region with the supplemental illumination for not less than 20 days. The treatment time can be flexibly determined according to the needs, and ratoon shoots and their tillers are made not complete photoperiod induction by supplemental illumination. After the harvest of main crop, the key technologies provided by the invention were utilized, such as leaving a low stubble, remaining a no-water layer or a thin-water layer with the water depth of not more than 3 cm within 7 days after the harvest of main crop under the premise that the water content of soil is greater than 60%. The fertilization amount already applied in the ratoon season accounts for 70% to 90% of the total fertilization amount in the whole growth period of the ratoon season accumulatively till the treatment under long-day conditions has been completed. Heavy fertilization will promote the ratoon shoots to produce a large number of tillers. The above-mentioned treatment may be repeated after the harvest of ratoon rice. The natural long day is used when it exists, and perform artificial illuminant supplement when it does not exist, so as to achieve the purpose of one-time of sowing and multi-years of harvesting.

The invention also provides ratoon rice produced by the methods. The invention discloses a variety breeding and cultivation method of ratoon rice. At present, there are two major problems in the production of ratoon rice, such as low yield and poor uniformity when matured. The root cause of low yield is that the growth period is too short, with the whole growth period of generally only 60-80 days. Moreover, vegetative growth and reproductive growth occur simultaneously, leaving almost no separate vegetative phase, resulting in the biomass for a single panicle is too small. The invention provides a method for prolonging the growth period of ratoon rice by screening photosensitive varieties of rice, cultivating ratoon rice under long day conditions and adopting corresponding cultivation measures, thereby not only improving the yield but also improving the mature uniformity of ratoon rice. Compared with the existing ratoon rice cultivation method, the invention may greatly improve the yield and quality of ratoon rice, and has good economic and social benefits.

BRIEF DESCRIPTION OF THE FIGURE

In order to illustrate the technical solutions in the embodiments of the invention or in the prior art more clearly, the drawings used in the descriptions of the embodiments or the prior art will be briefly described below.

DETAILED DESCRIPTION OF THE INVENTION

The invention discloses a variety breeding method for ratoon rice and a cultivation method for rice ratooning. Those skilled in the art can learn from the contents of the invention and appropriately adapt the process parameters to achieve the invention. Particularly, it should be noted that all such alternatives and modifications are obvious to those skilled in the art and are considered to be included within the invention. The method and the application of the invention have been described by the preferred embodiments, and it is obvious that the method and application described herein may be adapted or appropriately modified and combined by those skilled in the art to achieve the technologies of the invention and apply them, without departing from the content, the spirit and the scope of the invention.

The invention provides a method for prolonging the growth period of ratoon rice and increasing the maturation uniformity.

The invention provides a method for variety selection and cultivation of ratoon rice, comprising the following steps:
(1) Screening for rice varieties with suitable photosensitivity and good ratooning capacity;
(2) Cultivating the ratoon crop under a continuous long day condition, preventing or delaying the photoperiod induction of most low-node ratoon shoots and tillers thereof, thereby prolonging the growth period of ratoon season;
(3) Maintaining the continuous long day treatment in ratoon season for not less than 20 days, preferably, low stubbles are left, that is, the low-node ratoon buds of the last 4th node and below are retained, and the stubble is generally 8 to 15 cm in height;
(4) Promoting the germination of low-node ratoon shoots and producing a large number of tillers by fertilizer and water management, these low-node ratoon shoots and the tillers thereof will become the main source of the yield of ratoon rice.

In some specific embodiments of the invention, in step (1), the screening method comprises screening from existing varieties and breeding new varieties by genetic improvement methods.

In some specific embodiments of the invention, in step (1), the screened variety is preferably a low-node ratoon variety.

In some specific embodiments of the invention, in the step (2), the long day condition includes natural illumination or artificial illumination, and the artificial illumination is preferably performed in the middle of continuous dark cycles;

In some specific embodiments of the invention, in step (2), main crop is preferably cultivated under a long day condition from the completion of the photoperiod induction to the harvest of main crop, which is beneficial to prevent or delay the photoperiod induction of ratoon buds, especially low-node ratoon buds.

In some specific embodiments of the invention, in step (2), the continuous long day treatment of ratoon season preferably begins immediately from the harvest of main crop. It can also begin at any time. If it begins when the rice is not matured, and if the number of ratoon shoots before the treatment is ≤one third of the expected maximum number of shoots, only the management of fertilizer and water need to be enhanced to promote tillering. If the number of ratoon shoots is >one third of the expected maximum number of shoots, it is preferred to cut off the ratoon shoots, and the height is below the growth points of young panicle, with the stubble height general 5 to 10 cm. If ratoon rice is mature, it is the same as main crop.

In some specific embodiments of the invention, in step (2), it is preferred to leave low stubbles, so as to remove the germination ability of ratoon buds of the $3^{rd}$ node and above, and preserve the germination ability of last $4^{th}$ node and below nodes. Alternatively, perform rolling on stubbles, and only retain the germination ability of the low-node ratoon buds at the base.

In some specific embodiments of the invention, in step (2), the duration of ratoon season under the long day condition is preferably from 30 to 60 days.

In some specific embodiments of the invention, in the step (3), when the long day condition treatment is completed, the amount of fertilizer applied in the ratoon season accumulated accounts for 70%-90% of the total amount of fertilizer applied in the whole growth period of ratoon season. Ratoon season of rice should be fertilized after the 7 to 15 days' long day treatment to promote low-node ratoon shoots to germinate, producing a large number of tillers. During the period of about 10 days before the harvest of main crop, and during the period after harvest of main crop and the long day treatment not beginning immediately, the fertilization can be performed properly according to the needs to ensure the healthy vitality of ratoon buds and rice stubbles. In some specific embodiments of the invention, in the step (3), main crop is harvested to leave low stubbles. The no-water layer or a thin-water layer with a water depth not more than 3 cm is maintained within 7 days after harvest, with the premise that the soil moisture content is greater than 60%, which can reduce vacancy plants and promote low-node ratoon shoots tillering.

The proposed method of the invention is based on two known natural laws.

(1) Rice is a short-day crop, and its growth period is affected by the day length. The characteristic that rice varieties change the growth period thereof because of the influence of the day length is called photosensitivity. In the range of the duration of day suitable for growth and development, short days can shorten the reproductive phase, and long days can prolong the reproductive phase, and even cannot heal. Generally, the varieties in low-latitude regions have strong photosensitivity, while the varieties in high-latitude regions are insensitive or no-sensitive to the duration of day. The late rice varieties in the southern region have strong photosensitivity, while the early rice varieties have poor or no photosensitivity, and the photosensitivity of the mid-season rice is between the early rice and the late rice. In short, the growth periods of some rice are affected by the day length, which maybe serve as a rich resource and is the material basis of the invention.

Photosensitivity and long day are relative concepts. The rice varieties (or resources) with a critical day length of 13 h to 15 h are most abundant. If the photosensitive critical day length of a rice variety (or resource) is 13 h, then the day length of 13 h or longer is long day for the variety (or resource); if the photosensitive critical day length of a rice variety (or resource) is 14 h, then only the day length of 14 h or longer is long day for the variety (or resource).

The so-called long day is just a habit in the field. In fact, what is needed to complete the photoperiod induction is continuous dark cycles of a certain length. As long as the continuous dark cycle is shorter than the critical dark cycle required for the reproductive growth of photosensitive rice varieties, the photoperiod induction thereof can be inhibited or delayed. For example, a rice variety with a critical day length of 14 h requires a continuous dark cycle of 10 h per day to complete the photoperiod induction.

After a suitable short-day condition (long continuous dark cycle) is given to rice within a certain period of time to complete the floral induction, even if the rice afterwards is under an unsuitable photoperiod condition, the reproductive growth thereof will be continued instead of being reversed. This phenomenon is called photoperiod induction in botany. Therefore, in the case that the photoperiod induction has not been completed, it is only necessary to give a short-term illumination in the middle of the continuous dark cycle to prevent or delay the photoperiod induction of rice. This is very economical and environmentally friendly. As long as each dark cycle is shorter than the continuous dark cycle required for the photoperiod induction of the corresponding rice variety, reproductive growth can be inhibited or delayed. Even if the short dark cycle time added together is much greater than the required critical continuous dark cycle, the photoperiod induction is still inhibited or delayed.

The photosensitivity of the variety is not absolute and consistent. For example, some photosensitive varieties do not heal, and are even difficult to complete the photoperiod induction under long day conditions. Some photosensitive varieties can heal under long day conditions, but this takes a long time. However, it is a common law that the growth period of the photosensitive variety can be prolonged under long day conditions, which is the theoretical and material basis to establish the invention. For the differences between photosensitive varieties, it is possible to explore individualized application methods according to their characteristics, which may have unexpected gains.

Figure 1:
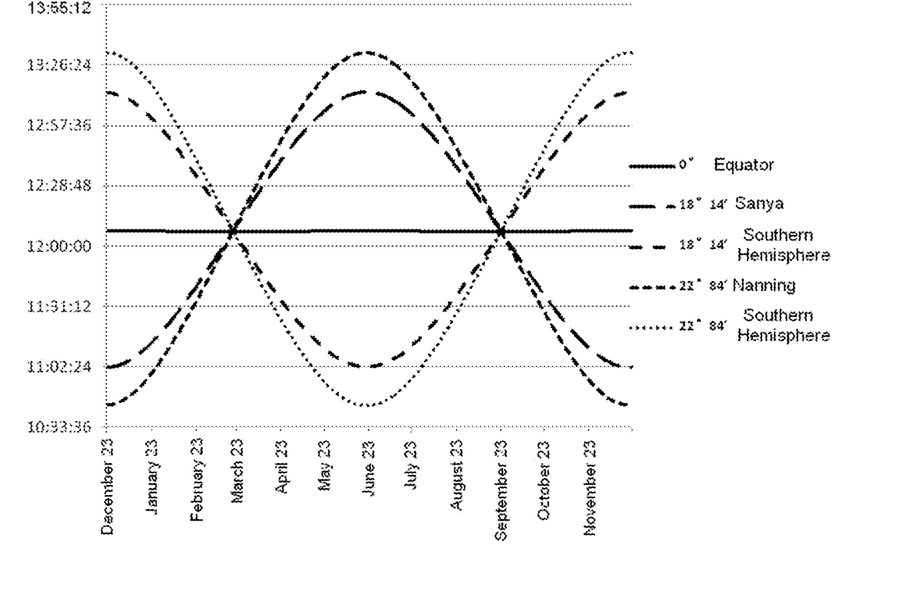
FIG. 1 is the change curve of the natural day length for representative regions of the world.

(2) In tropics and subtropics suitable for the application of the invention, the annual natural day length changes parabolically. Ratoon rice has higher requirements on illumination and temperature conditions, and in particular, the invention prolongs the reproductive phase of ratoon rice. Therefore, the most suitable application area of the invention is a double-season rice area, and an ecological zone with better illumination and temperature conditions that the rice can be planted on an annual basis. It mainly includes tropics and subtropics, but some of the mountainous areas with poor illumination and temperature conditions are not suitable for planting. In tropics and subtropics, the day length every day changes regularly during the year, and there is basically no change between years. For example, the day length and the night length are the same on same latitude, and the sunrise time and the sunset time are the same on same latitude. The vernal equinox and the autumn equinox have day and night equally. In the summer half year, the day is long and the night is short. In the winter half year, the day is short and the night is long. In the same place, there are two days in a year having the same day length (the night length), and the same sunrise (sunset) time. These two days are two dates having equal number of days from the summer solstice or from the winter solstice. The global day length and night length variations increase progressively from the equator (0) to the north and south sides (up to 24 hours), and the annual natural day length changes parabolically. The equatorial region can be seen as a special parabola with the minimal variation. Plot the actual day length observation data in 2017 at equator (0 latitude, typical tropics); Nanning, China (north latitude 22°48', the junction of tropics and subtropics); southern latitude 22°48', southern hemisphere; Nanjing (north latitude 32°02', the north end of subtropics); southern latitude 32°02', southern hemisphere, and it can be clearly seen that the day length changes parabolically in the year (FIG. 1). The trend of changes of the southern hemisphere is similar to that of the northern hemisphere.

The above two natural laws are well known to those skilled in the art.

Although it has long been recognized that when the day length is greater than the critical day length of the photosensitive variety, the photosensitive variety is difficult to complete the photoperiod induction, and the reproductive growth thereof is slow or completely stopped, and the growth period is greatly prolonged. However, to date, the use of photosensitivity to prolong the growth period of ratoon rice has not been publicly reported. It mainly has the following problems. First, the photosensitive variety has a long growth period. Even if the photosensitive variety is cultivated as a ratoon rice, the natural day length after harvest of main crop is generally shorter than the critical day length of the variety, and it is difficult to observe the prolongation of the growth period of ratoon rice. Second, the differentiation progress of young panicle from ratoon buds at different nodes is inconsistent. Even under long day conditions, the growth of ratoon rice is still not even and regular. Therefore, although the rice planting history has been for thousands of years, the invention has not been reported in any literature, and there is no practical application, therefore it is not obvious.

In order to prolong the growth period of ratoon rice by a long-day condition, the following conditions must be met. First, a long-day condition is given when ratoon buds have not completed the photoperiod induction. But at present, some varieties completed the photoperiod induction of main crop when given only about 15 days of short day, then they are under long-day conditions all the time, and there are still a few high-node ratoon shoots healing in 40 days, indicating that the photoperiod induction of some high-node ratoon buds is almost synchronous with that of main crop. Second, a long day is given after harvest of main crop, and corresponding cultivation and management measures are taken during the harvest, for example, using low-node ratoon varieties, leaving low stubbles to remove ratoon buds of last $3^{rd}$ node and above, rolling rice stubbles, and so forth, to promote the low-node ratoon buds germinate into seedlings and inhibit the high-node ratoon buds germinate into seedlings. Early and heavy fertilization, especially nitrogen fertilization is carried out after harvest of main crop to promote low-node ratoon shoots to produce a large number of tillers, which have new independent root systems. Since the young ear differentiations of low-node ratoon buds are slower than that of high-node ratoon buds, some low-node ratoon buds and all the tillers thereof have not completed the photoperiod induction. Their growth period can be greatly prolonged under long-day conditions, and until the long-day conditions are removed, the low-node ratoon buds and all the tillers thereof simultaneously initiate the reproductive growth process, and the maturation uniformities of them improve greatly. This method mainly utilizes low-node ratoon shoots and the tillers thereof. These ratoon shoots and the tillers thereof have new root systems and grow fast. If the growth period is sufficient and the fertilizer and water management level is high, the production capacities of these ratoon shoots and the tillers thereof are strong, and can reach or even exceed the level of double-season late rice in the same region. For high-node ratoon buds with no independent root systems, if the growth period is prolonged, the biomass of the high-node ratoon buds will also increase. However, most of the high-node ratoon buds have completed the photoperiod induction, which is likely to lead to an uneven mature stage of ratoon rice.

The method adopted by the invention utilizes the photosensitivity of rice to prolong the growth period of ratoon season and improve the maturation uniformity. In order to achieve the above technical object, the invention provides a method for prolonging the growth period of ratoon season of rice and improving the maturation uniformity, which comprises the steps of: (1) screening for the rice varieties with suitable photosensitivity and good ratooning capacity; (2) making the ratoon season under a continuous long-day condition for not less than 20 days, thereby prolonging the growth period of ratoon season; the ratoon season under the long-day condition can begin immediately from the harvest of main crop, or the ratoon season can be under a continuous long-day condition after a period of time from the harvest of main crop. The long day is a relative concept, and if the day length longer than the critical day length of a certain variety, then the illumination is the long day of the variety. The photoperiod induction of this rice variety is difficult to complete or greatly delayed under long-day conditions. (3) Promoting low-node ratoon shoots germinate into a large number of tillers by fertilizer and water management measures. These low-node ratoon shoots and the tillers thereof will become the main source of the economic yield of ratoon rice.

In the invention, the variety is a carrier with a very rich connotation, including rice quality, yield, resistance, growth period and the like. It is restricted by ecological conditions and farming systems, and is also affected by social needs. Moreover, as time goes by, people's requirements for varieties are also changing. When applying the invention, people should comprehensively consider main crop and ratoon rice according to the local actual conditions to better meet the market demand and obtain greater economic and social benefits. Food security is related to national security. In order to standardize and guide researchers and producers, rice researchers, producers and relevant government departments will develop a unique regional test system around the invention before the invention is widely used in production. This is well known to those skilled in the art. Therefore, the invention only discusses the unique technical features of the invention.

Among them, rice varieties with suitable photosensitivity can be obtained by conventional breeding or molecular design or transgenic methods, or by screening suitable varieties from existing varieties or resources. It can be either conventional rice or hybrid rice. As of 2006, the South China region has developed 146 (times) approved photosensitive hybrid rice combinations, and significant progress has been made in the breeding of interactive photosensitive sterility lines and restoring lines. The invention can learn from the valuable conventional breeding experience accumulated in these decades when breeding photosensitive varieties. As of 2017, a number of major genes related to photosensitivity have been cloned one after another, and the molecular mechanism is gradually becoming clear. Some molecular biologists have begun to explore the effects of some major photosensitive genes in rice on the growth period of rice. The above research outcomes lay a good foundation for the breeding of new photosensitive varieties through molecular design.

The screened varieties must have strong ratoon capacity, preferably low-node ratoon varieties similar to japonica rice and wild rice. However, wild rice cannot be directly applied in production. Indica rice is generally not a low-node ratoon variety, and it is possible to breed low-node ratoon Indica rice varieties by hybridizing Indica rice with japonica rice or wild rice. The strong ratoon ability means that the ratoon bud has strong vitality, and if the ratoon bud has low vitality, it is likely to cause a large number of vacancy plants in the case of leaving low stubbles. Most of the low-node buds have not completed the photoperiod induction, and the uniformity is good. The low-node buds are close to the soil, and can germinate new root systems and have great productivity potential. The low-node buds can especially produce a large number of effective tillers quickly with new root systems. These low-node ratoon shoots and the tillers thereof will be the main source of the yield of ratoon rice as described in the invention.

The determination of the intensity of photosensitivity should be determined according to the ecological conditions and production needs of different regions. Under the premise of safe production, it is necessary to ensure that ratoon rice has a long growth period to obtain the high yield, and also to ensure a bumper harvest of main crop.

The invention provides a method for practicing the invention using natural day conditions. By selecting suitable photosensitive rice varieties and arranging the sowing time, main crop can be made to successfully complete the photoperiod induction when the day length is shorter than the critical day length of the variety to ensure that main crop matures on time. The ratoon season can be under natural long-day conditions after harvest of main crop, and preferably, be under long-day conditions immediately after the completion of photoperiod induction of main crop. The specific method includes that if the growth period of main crop is too long, it can be solved by the following measures: breeding the varieties with short basic vegetative phase, or using the greenhouse to breed seedlings at low latitudes in advance, or breeding the varieties with high tolerance to low temperature at the seedling stage and sowing in advance, and so on. It is also possible to make comprehensive utilization of the above methods to make full use of the growing season on the basis of ensuring the safe production of main crop. The method has strict requirements on the critical day length of rice variety, and requires it to not only ensure that main crop and ratoon rice can complete the photoperiod induction and maturation on time, but also ensure that the ratoon season has sufficient long day time. However, the use of natural illumination to prolong the growth period of ratoon rice is economic and environmentally friendly.

The invention provides a method for inducing young ears differentiation for main crop using artificial shading. If the photosensitivity of main crop is too strong to complete the photoperiod induction at a predetermined time, the shading treatment can be performed for 8 to 30 days and the daily illumination time is 9 to 10 hours. The treatment time and the day length vary from varieties to varieties and must be determined by prior testing. Generally, the shorter the treatment time and the longer the day length, the smaller the effect on rice. But too short treatment time and too long day length may cause a failure in photoperiod induction.

The invention provides a method for creating a long-day condition for the ratoon season of rice using an artificial light source. The method comprises directly giving the illumination with an illuminance of not less than 1000 Lx when it's getting dark, and sum of the illumination time and the natural illumination time per day added together is larger than the critical day length of the rice variety planted.

Further, the invention provides a preferred long-day method. The method comprises providing the illumination with an illuminance of not less than 1000 Lx in the middle of the continuous dark cycle for not less than 30 minutes per day. Since different varieties have different responses to illumination, it is necessary to explore the shortest effective treatment time and the minimum effective treatment illuminance according to the specific varieties, thereby saving energy, reducing costs and reducing environmental impact.

Artificial shading and artificial light source supplemental illumination must increase the input, and it may have some adverse effects on the environment, but it can expand the application range of the invention and increase the degree of freedom.

The continuous long-day treatment of ratoon season of rice preferably begins immediately from the harvest of main crop. It can also begin after a period of time from the harvest of main crop. If begin when the rice is not matured, and if the number of ratoon shoots before the treatment is ≤one third of the planned maximum number of seedlings, only the management of fertilizer and water need to be enhanced to promote tillering. If the number of ratoon shoots is >one third of the planned maximum number of seedlings, it is preferred to cut off the ratoon shoots, and the principle for determining the height of the stubble is to remove the growth points of young ears of ratoon rice, and the stubble height generally is 8 to 15 cm. If ratoon rice is mature, it is the same as main crop, and harvest directly and leave low stubbles.

The invention provides a method for promoting the germination of low-node ratoon buds. The method comprises breeding low-node ratoon varieties; leaving low stubbles, removing ratoon buds of the last $3^{rd}$ node and above nodes, and preserving ratoon buds of the last $4^{th}$ node and below nodes, the stubble height generally is 8 to 15 cm and differs slightly between the varieties; or rolling rice stubbles to promote the germination of ratoon buds at the base. All of the above measures have only one purpose, that is, to promote low-node ratoon buds to germinate, to grow new root systems, and to produce a large number of tillers with new root systems.

After main crop has completed the photoperiod induction, it is preferably under long-day conditions as soon as possible to prevent or delay the completion of the photoperiod induction of the low-node ratoon buds.

Determining the stubble height is the key technical link of ratoon rice. The order for differentiation of young ears of ratoon buds of rice stubble is generally faster in high nodes than in low nodes. At the time of the harvest of main crop, the high-node ratoon buds generally completed the photoperiod induction, and only a few of low-node ratoon buds may have completed the photoperiod induction. Giving a long-day condition immediately after the completion of the photoperiod induction of main crop may delay the photoperiod induction of ratoon buds. Said high nodes refer to the last $2^{nd}$ node and the last $3^{rd}$ node, and the last $1^{st}$ node of ratoon buds generally do not germinate. The low nodes refer to the last 4$^{th}$ node, the last 5$^{th}$ node and below nodes. As some varieties have last 6$^{th}$ node, and some varieties do not have. The advantage of leaving high stubbles is that there are fewer vacancy plants and more tillers. The disadvantage of leaving high stubbles is that the high-node seedlings generally have completed the photoperiod induction, which will make a gap between the growth period of high-node shoots and that of low-node shoots. Since the high-node seedlings matured too early, it makes no contribution to the yield basically, what's more, the ratoon shoots thereof and old stubbles and stalks will have more or less effect on the germination and tillering of the low-node ratoon buds, and sometimes even have serious impacts. The advantages of leaving low stubbles are that most of the ratoon shoots and all the tillers have not completed the photoperiod induction, the development progress is consistent, and the maturation uniformity is good, and the low-node ratoon buds do not affected by the old stubble and the high-node ratoon shoots. The disadvantage of leaving low stubbles is that the germination capacity of low-node ratoon buds of some varieties is weak, which is easily to cause vacancy plants. Therefore, what is needed is to select varieties with strong ratoon ability, and preferably leave low stubbles.

The invention provides a fertilization method for ratoon rice. When the long-day condition treatment is completed, the amount of fertilizer applied in the ratoon season accumulated accounts for 70%-90% of the total amount of fertilizer applied in the whole growth period of ratoon season. After harvest of main crop, the long-day treatment carried out immediately in some cases, and in other cases, the long-day treatment carried out after a while. Fertilization principle: The long-day treatment period is equivalent to the tillering stage of main crop, and the growth is quite strong. When the long-day treatment is completed, the amount of fertilizer applied in the ratoon season accumulated accounts for 70%-90% of the total amount of fertilizer applied in the whole growth period of ratoon season. Other aspects of the invention, such as, main crop should be down well in prevention and control of diseases and insect pests, fertilizer and water management to ensure the health of rice stubbles and the strong vitality of ratoon buds; the growth period of main crop and ratoon rice should be arranged reasonably according to the crops for rotation, the illumination and temperature conditions, etc. to obtain the best results, and the like; different cultivation and management methods should be adopted in different regions due to the differences in soil fertility, planting targets and cultivation practices; and the like; all these are obvious to those skilled in the art and will not be described again.

The beneficial effects of the invention are:
(1) The invention provides a method for variety screening and cultivation of ratoon rice. Compared with ordinary ratoon rice, the invention can prolong the growth period of ratoon rice and greatly increase the yield level per unit area; at the same time, it can improve the maturation uniformity and improve the quality of rice. In short, compared with ordinary ratoon rice, the invention can greatly increase the yield and quality. Therefore, it has good economic and social benefits.
(2) By utilizing the invention, in subtropics where the illumination and temperature resources are abundant and two seasons of rice can be planted in a year, it is possible to harvest two seasons with one sowing, and the yield and quality of ratoon rice can be comparable to that of double-season late rice, and even better. Compared with ordinary late rice, the invention, when applied in production, can save seeds, save labor, reduce fertilizer, reduce soil and water loss, and has good economic and social benefits.
(3) By using the invention, in tropics where the illumination and temperature resources are abundant and rice can be planted all year round, when combined with artificial illumination or shading treatment, it is even possible to achieve multi-year harvesting with one sowing.
(4) The wide application of the invention will change the rice planting pattern for thousands of years, which is conducive to reducing the production cost of rice, and achieving an increase in production, cost saving, and efficiency.

The varieties, reagents and fertilizers used in the ratoon rice breeding methods and the cultivation method of ratoon rice provided by the invention can be obtained commercially or from related scientific relevant research institutes.

The invention is further illustrated below in combination with the embodiments.

The invention is suitable for use in areas with good temperature and illumination conditions in tropics and subtropics. These areas can be divided into three main types. First is area where rice can be planted all year round and the variation in day length is small. These areas are all in tropics, such as the equator and its vicinity. The second is area where rice can also be planted all year round but the day length varies greatly. These areas are mainly in tropics, such as Hainan and the like. The third is area where rice cannot be planted in winter and the day length varies greatly. These areas are mainly in subtropics, such as Guangxi, Hunan and the like. Therefore, specific embodiments of the invention are exemplified by the equatorial region, Sanya, Hainan, and Nanning, Guangxi.

Example 1 Implementation of the Invention in the Equatorial Region

The illumination and temperature resources in the equatorial region are abundant, and the day length is relatively stable. The annual day length is between 12 hours and 6 minutes and 12 hours and 7 minutes. The variety with a critical day length shorter than 12 hours and 6 minutes can be screened or bred. For example, a variety with a photosensitivity similar to that of RH. The critical day length of RH is about 11 hours and 28 minutes. The photoperiod induction can be broken by shading treatment. Shaded for 8 to 30 days, and gave 9-10 hours of natural illumination every day. After the completion of the photoperiod induction, turned into natural illumination. After harvest of main crop, by using the key technologies provided by the invention, such as, leaving low stubbles, the no-water layer or a thin-water layer with a water depth not more than 3 cm was maintained within 7 days after harvest of main crop, with the premise that the soil moisture content was greater than 60%. When the long-day condition treatment was completed, the amount of fertilizer applied in the ratoon season accumulated accounted for 70%-90% of the total amount of fertilizer applied in the whole growth period of ratoon season. Early and heavy fertilization promoted the ratoon shoots to produce a large number of tillers, and after harvest of main crop 30-60 days, chose the opportunity to shading again according to the specific circumstances, so that the ratoon shoots can smoothly enter the reproductive growth stage. After harvest of ratoon rice, the above treatment can be repeated to achieve the purpose of multi-year harvesting with one sowing. The photosensitive variety with a critical day length longer than 12 hours and 7 minutes can also be selected. After harvest of main crop, supplied illumination such that partial ratoon shoots and all the tillers thereof cannot complete the photoperiod induction. The illumination was supplied for 30 to 60 days, and the treatment time was flexibly determined as needed. By using the key technologies provided by the invention, such as, leaving low stubbles, the no-water layer or a thin-water layer with a water depth not more than 3 cm was maintained within 7 days after harvest of main crop, with the premise that the soil moisture content was greater than 60%. When the long-day condition treatment was completed, the amount of fertilizer applied in the ratoon season accumulated accounted for 70%-90% of the total amount of fertilizer applied in the whole growth period of ratoon season. Early and heavy fertilization promoted the ratoon shoots to produce a large number of tillers. For example, after harvest of ratoon rice, the above treatment can be repeated to achieve the purpose of multiple harvesting with one sowing.

Due to the abundant illumination and temperature resources in the equatorial region and rice can be planted on an annual basis therein, the use of the invention can achieve multi-year planting with one sowing for rice. The vicinity of the equator is similar to the equatorial region in illumination and temperature resources, and can be used for reference in the equatorial region. Taking the planting of the variety with a similar photosensitivity to RH in the vicinity of the equator as an example, any region with the shortest day length above the critical day length of RH can be used in a similar way to the equatorial region. Similarly, in the vicinity of the equator, the photosensitive variety with a critical day length longer than the annual day length thereof can also be used. It can be achieved by the key technologies provided by the invention, such as supplemental illumination, leaving low stubbles, and the like, and can refer to the method used in the equatorial region. The day length in the vicinity of the equator has a small fluctuation. The photosensitive variety with a critical day length between the natural longest day and the shortest day can be selected. The natural short day can be used to complete the photoperiod induction and the natural long day can be used to prolong, prevent or delay the photoperiod induction, which is the most economical and environmentally friendly. For details, it can refer to the method for implementing the invention in Nanning, Guangxi.

Simulate the Shading Test in the Equatorial Region

Due to the limitations of the conditions, the invention simulates the tests of the equatorial region in Nanning. Specific practice: Selected the rice resource RH with strong photosensition, and the critical day length thereof is about 11 hours and 28 minutes. The natural day length in the equatorial region is longer than the critical day length of RH. The natural day length in Nanning from February 18 to October 23 is longer than the critical day length of RH. The tests of planting ratoon rice with strong photosensitive rice varieties in the equatorial region can be simulated. RH is a strong photosensitive rice resource from Southeast Asia, and its agronomic traits are poor. This experiment only verifies that the invention can prolong the growth period of ratoon rice and improve the maturation uniformity, without considering yield and other traits. Prolonging the growth period and improving the maturation uniformity are the basis for realizing the high yield of ratoon rice. Those skilled in the art can select the newly-developed strong photosensitive excellent varieties with reference to the present embodiment, and learn from the cultivation method of the invention to realize multi-year harvesting with one planting.

Main crop in Nanning was sown on February 26 and transplanted on April 3. From May 10, the shading treatment was performed using black and white film, with white facing up and black facing down. Only 9 hours of natural illumination was given per day for 30 consecutive days. For medium fertility soil, 40 kg of 25% rice special compound fertilizer per mu was applied as base fertilizer. 7 days after transplanting, the herbicide was applied in combination, followed by 7.5 kg of urea per mu. 7 kg of potassium chloride per mu was applied at the beginning of young ears differentiation on May 20. Healing began on June 12 and the harvest was on July 15. Left low stubbles (about 12 cm), kept the soil moist but no water layer can be seen for the first 10 days after harvest, and did the drainage work in rainy weather. On the 11th day, shallow water was applied, and 30 kg of 25% rice special compound fertilizer and 7.5 kg of urea per mu were applied. In the later stage, the dry and wet separation promoted tillering. On August 15, when the total number of seedlings per mu reached 200,000 seedlings, drained off water timely to make the field dry in the sun and control the seedlings. On August 25, the shading treatment was performed using black and white film, with white facing up and black facing down. Only 9 hours of natural illumination was given per day for 30 consecutive days. 5 kg of potassium chloride per mu was applied at the beginning of young ears differentiation on September 5. Healing began on October 3 and the harvest was on November 20. The whole growth period of ratoon season was 127 days. Except for a very small number of early ears (<5%), the healing was relatively uniform and the maturity was relatively consistent.

TABLE 1

The growth period of shading treated main crop and ratoon crop of RH

| Type | Duration of harvest (day) | Whole growth period (day) | Early panicle rate (%) |
|---|---|---|---|
| main crop | 107 | 137 | — |
| ratoon crop | 80 | 127 | 2.1% |

The whole growth period of ratoon crop in this test reached 127 days, far exceeding the 60-80 days of conventional ratoon rice. In fact, by applying the invention by shading treatment, the growth period of ratoon season can be freely adjusted as needed. In the equator and suitable tropics near the equator, after harvest of ratoon rice, the cultivation and management methods of ratoon rice can be continued to achieve multiple harvesting with one sowing.

This embodiment not only simulates the shading planting on an annual basis in tropics, but also has guiding significance for local areas in Nanning and similar areas. It takes time for the earth to warm up and cool down. For example, taking June 21 with the longest day length as the midpoint, the time suitable for rice growth in early period is short (from the end of February to June 21), and the time suitable for rice growth in later period is long (from June 21 to November 20). In order to make full use of the illumination and temperature conditions, a strong photosensitive variety with a shorter critical day length (but longer than the critical day length of RH and no shading is needed during the ratoon season) can be selected. For example, a variety with a critical day length corresponding to the natural day length on around August 20 can be selected. According to the change rule of day length, the natural day length from April 20 to August 20 is longer than the critical day length of the variety.

If sown at the end of February, the general variety will be difficult to complete the photoperiod induction before April 20. Therefore, the shading treatment of this embodiment can be employed, and the harvest was in the mid and late July. After August 20, the natural day length is shorter than the critical day length, and ratoon rice can successfully complete the photoperiod induction, no need for artificial shading anymore. Ratoon rice was full heading at the end of September and harvested in mid-November, and it can make good use of the annual illumination and temperature resources. Only the modes and methods for implementing the invention are discussed herein, and in actual applications, adjustments can be made according to variety characteristics, farming systems, social needs, and the like. These are undoubtedly obvious to those skilled in the art.

Supplemental Illumination Test in the Simulated Equatorial Region

Due to the limited conditions, the situation where the natural day length is shorter than the critical day length of the photosensitive varieties in equatorial region was simulated in Nanning.

Tested variety: Lingliangyou 472. Treatment 1: 1 hour of illumination was supplied immediately when it's getting dark every day, the illuminance at the stump of a plant was 1000 Lx, and the treatment time was 30 days (August 1-August 30); treatment 2: 30 minutes of illumination from 23:30-24:00 was supplied every day, the illuminance at the stump of a plant was 1000 Lx, and the treatment time was 30 days (August 1-August 30); treatment 3: no supplemental illumination. This embodiment only verifies the effect of supplemental illumination to prolong the growth period and improve the maturation uniformity, and does not measure the production.

Sown on February 26 and transplanted on April 3. The fertilizer and water management measures in the field were the same as in Example 1. Harvested on August 1. Left low stubbles (about 12 cm). Ratoon rice with supplemental illumination began to heal on about September 28, with only a very small amount (<5%) of the ratoon shoots healing in advance, and the uniformity was good. Ratoon rice without supplemental illumination (conventional ratoon rice) began to heal on August 28, and the maturation uniformity was poor.

TABLE 2

The growth period and uniformity of Lingliangyou 472 with different illumination treatments

| type | Duration of harvest (day) | Whole growth period (day) | Early panicle rate (%) |
| --- | --- | --- | --- |
| supplemental illumination treatment 1 | 59B | 102B | 2.5 |
| supplemental illumination treatment 2 | 60B | 103B | 2.7 |
| no supplemental illumination | 28A | 71A | poor maturation uniformity |

Note:
Different letters in the same column indicate that the difference is extremely significant (P < 0.01).

This embodiment shows that the supplement of illumination of the same length has the same effect of breaking the photoperiod induction. The supplemental illumination time in treatment 1 is longer than that in treatment 2, because that the natural day length was shortened by more than 30 minutes in the 30 days of the treatment, therefore the supplemental illumination time was extended for the sake of safety. It can also be seen from this embodiment that the method of treatment 2 to break the dark cycle was more efficient. Moreover, it was possible to explore shorter supplemental illumination time based on differences between varieties.

Rice variety breeding involves growth period, rice quality, yield, resistance, etc.; and the sowing schedule involves climate, crops for rotation, etc. There are differences in tastes and habits between every place, every nation, and every country. Therefore, rice production is quite complicated. These contents are obvious to those skilled in the art and will not be described again. Both the present embodiment and the following embodiments focus only on the key technologies unique to the invention.

Example 2 Implementation of the Invention in Sanya, Hainan

Sanya is located at low latitude and belongs to a tropical maritime monsoon climate zone with abundant illumination and temperature resources. The annual average temperature is 25.7° C., and the month with the lowest temperature is January, with an average of 21.4° C. It is known as the "natural greenhouse". The day length is the longest on June 21 every year, which is 13 hours and 13 minutes; and the day length is the shortest on December 22 every year, which is 11 hours and 2 minutes. The day time of the whole year is 2534 hours. Rice can be planted on an annual basis.

The temperature and illumination conditions in Sanya are good, and the sowing time is relatively free. In theory, without considering other factors, there are not less than 20 days with the time longer than the critical day length of a photosensitive variety in Sanya, that is, the critical day length is shorter than 13 hours and 10 minutes (June 11 to July 1). The variety can apply the invention. Long-day treatment for 20 days is only the minimum of application of the invention, and it is preferably to treat for 30 to 60 days. However, the growth period of ratoon rice is not the longer the better. If the growth period is too long, in one aspect, it can result in the occupation of land, the long management time of fertilizer, water, and the control of pests and diseases, leading to a decline in economic benefits, and in another aspect, it will affect the arrangements of crops for rotation for main crop and other crops. In the exclusion of certain special circumstances, the economic benefit of a long-day treatment of not more than 2 months for the ratoon season is generally better. In addition, the booting and grouting in the late of main crop can be under long-day conditions for generally about 2 months, therefore, and the total time longer than the critical day length of the photosensitive variety is preferably not more than 4 months. The critical day length is longer than 12 hours and 39 minutes (April 21 to August 21). Therefore, if a natural illumination condition is used, a photosensitive variety with a critical day length between 12 hours and 39 minutes and 13 hours and 10 minutes should be selected in Sanya.

Assuming that the variety with a critical day length of about 12 hours and 47 minutes has been screened, the day length in Sanya from May 1 to August 11 is greater than the critical day length of the variety. Through reasonable sowing schedule, it is possible to make the variety complete the photoperiod induction before April 20 and harvest main crop around June 20. After harvest of main crop, by using the key technologies provided by the invention, such as, leaving low stubbles, the no-water layer or a thin-water layer with a water depth not more than 3 cm was maintained within 7 days after harvest of main crop, with the premise that the soil moisture content was greater than 60%. When the long-day condition treatment was completed, the amount of fertilizer applied in the ratoon season accumulated accounted for 70%-90% of the total amount of fertilizer applied in the whole growth period of ratoon season. Early and heavy fertilization promoted the ratoon shoots to produce a large number of tillers. After August 11, it would be transferred into the young ears differentiation stage. Healing began in early September and the harvest was in the early and mid-October. If it is necessary to further prolong the growth period of ratoon rice, sowing in advance or breeding of similar photosensitive varieties with short growth period can be carried out to make main crop harvest as early as around June 10. After harvesting of ratoon rice, since the natural day length is shorter than the critical day length of the variety, it can be re-sown in the coming year, or it can refer to the situation in equatorial region, for example, supplemental illumination can be carried out to make the tillers of the ratoon shoots cannot differentiate into young ears. The supplemental illumination time was not less than 20 days and can be determined flexibly according to needs. By using the key technologies provided by the invention, such as, leaving low stubbles, the no-water layer or a thin-water layer with a water depth not more than 3 cm was maintained within 7 days after harvest of main crop, with the premise that the soil moisture content was greater than 60%. When the long-day condition treatment was completed, the amount of fertilizer applied in the ratoon season accumulated accounted for 70%-90% of the total amount of fertilizer applied in the whole growth period of ratoon season. The above-mentioned treatments can be repeated after harvest of ratoon rice. When there was natural long day, natural long day was used, and when there was no natural long day, artificial illumination was used.

The Tests of Ratoon Rice to which the Invention Applied

The rice resource RH with strong photosensitivity was as the test material, and the critical day length thereof is about 11 hours and 28 minutes. The natural day length in Sanya from February 10 to November 1 is longer than the critical day length of RH. In 2017, sowing was on December 5 and transplanting was on December 25. The photoperiod induction was completed in early February. Healing began from March 3, and maturation was on April 10. Left low stubbles, kept the soil moist but no water layer can be seen within one week after harvest, and did the drainage work in rainy weather. Fertilization and field management were based on local farming practices. Since the natural illumination from April 11 to November 1 is long day for RH, the time is too long. Shading treatment was carried out on June 12, after 2 months of long-day treatment, and only 9 hours of natural illumination was given per day for consecutive 30 days. See Technical Example 1 for specific technical details. Healing began on July 18, and the first season ratoon rice matured and harvested on August 20. After harvest of ratoon season, the key technology of the invention continues to be applied. Healing began on December 2. On Jan. 8, 2018, the second season matured and harvested, and left high stubbles. From January 8 to February 9, the natural day length is short day for RH. On February 10, it re-entered into the natural long-day conditions of RH. At this time, ratoon rice had produced enough ratoon shoots, and the photoperiod induction had been basically completed, and the conventional ratoon rice was harvested for one season. Healing of the third season conventional ratoon rice began on February 20, and they matured and harvested on March 26. Low stubbles were left, and the key technologies of the invention were applied. No booting was observed in the field on August 18, so the experiment was terminated.

TABLE 3

Growth period of main crop and the ratoon crop of RH

| type | Duration of harvest (day) | Whole growth period (day) | Early panicle rate (%) |
|---|---|---|---|
| main crop | 88 | 125 | uniform |
| the first ratoon rice of the present invention | 100 | 133 | 2.7 |
| the second ratoon rice of the present invention | 104 | 140 | 1.9 |
| the third ratoon rice of conventional method | 43 | 77 | un-uniform |
| the fourth ratoon rice of the present invention | had not began healing until day 143 | | 3.1 |

In this region, since the rice can be planted on an annual basis, and the day length has a certain variation, the manner in which the invention is applied is various, as can be seen from the examples. Natural illumination can be used to harvest two seasons with one season planting. It can also refer to the situation in equatorial region to achieve multi-year harvesting with one planting through the measures of shading and supplemental illumination. These contents are obvious to those skilled in the art and will not be described again.

Example 3 Implementation of the Invention in Nanning, Guangxi

Nanning is located on the south side of the Tropic of Cancer and belongs to a humid subtropical monsoon climate. The annual average temperature is about 21.6° C. The extreme maximum temperature is 40.4° C., and the extreme minimum temperature is −2.4° C. The illumination and temperature resources are abundant. A significant difference between Nanning and tropics such as the equator and Sanya is that rice cannot be planted on an annual basis.

Early rice in Nanning was usually sown at the end of February and harvested at the beginning of July, and the longest day of the year appears on June 21. Due to the limitation of early illumination and temperature conditions, it was suitable to arrange main crop to be harvested generally at the end of June and early July. If the harvest was too early, it was easy to cause the insufficient growth period and low yield of main crop. Ratoon rice was treated with the long-day treatment for not less than 20 days using the technology of the invention. Performing calculation according to harvesting main crop on June 30. After 20 days (July 20), the natural day length is 13 hours and 20 minutes, thus the critical day length of the selected photosensitive variety should be shorter than 13 hours and 20 minutes. Considering that in early February, artificial greenhouses or low-latitude areas (such as Hainan) may be used for seedling breeding in advance, and seedling transplanting may be carried out at the end of February and early March, the temperature in the early stage was low, thus it was relatively early to complete photoperiod induction before April 20. Therefore, the critical day length of the selected photosensitive variety must be longer than 12 hours and 47 minutes (the natural day length on April 20). Therefore, with the condition that the invention was realized by natural illumination, the critical day length of the photosensitive variety selected in Nanning area was suitable to be 12 hours and 47 minutes to 13 hours and 20 minutes. At the same time, it was necessary to ensure that main crop may be safely harvested at the end of June and early July.

A variety with a critical day length of about 13 hours and 10 minutes may be screened or bred, and the natural day length in Nanning from May 12 to July 31 is greater than the critical day length of the variety. Through reasonable sowing schedule, the variety can be made to complete the young ears differentiation before May 12 and main crop can be made to be harvested before June 30. After harvest of main crop, by using the key technologies provided by the invention, such as, leaving low stubbles, the no-water layer or a thin-water layer with a water depth not more than 3 cm was maintained within 7 days after harvest of main crop, with the premise that the soil moisture content was greater than 60%. When the long-day condition treatment was completed, the amount of fertilizer applied in the ratoon season accumulated accounted for 70%-90% of the total amount of fertilizer applied in the whole growth period of ratoon season. Early and heavy fertilization promoted the ratoon shoots to produce a large number of tillers. After August 1, it would be transferred to the young ears differentiation stage, healing began in early September, and the harvest was in the early and mid-October. If it is necessary to further prolong the growth period of ratoon rice, it may be achieved by sowing in advance or breeding of similar photosensitive varieties with short growth period. However, due to the limitations of temperature and illumination conditions, the adjustable range was relatively small.

Subtropics such as Nanning and Changsha are rich in light and temperature resources, but rice cannot be planted on an annual basis. Natural illumination can be used to harvest two seasons with one season planting. It can also refer to the situation in equatorial region to select the photosensitive varieties with suitable critical day length through the measures of shading and supplemental illumination. If a variety with strong sensitization is used, the photoperiod induction of main crop will be broken by shading treatment. Ratoon rice will make full use of the illumination and temperature resources in the second half of the year. If ratoon rice is under natural illumination conditions shorter than its critical day length, its growth period can also be prolonged by supplemental illumination. The implementation of the invention will be more flexible and diverse by means of artificial shading and supplemental illumination. These contents are obvious to those skilled in the art and will not be described again.

Test in Nanning

Test materials: photosensitive variety Lingliangyou 472, Guoshen Rice 2010001, a double-season late rice in South China. The following tests were conducted with Lingliangyou 472 as the test material.

The test protocol to which the invention applied repeated 3 times, and the average value was taken.

Main Crop

Sowing date: February 1. Location: Wanning, Hainan. Transplanting date: February 26.

Healing beginning date: May 20. Yellow ripening date: June 26. Whole growth period: 146 days.

Ratoon Crop (Low Stubble)

Healing beginning date: August 28. Yellow ripening date: October 12. Whole growth period: 108 days.

The conventional ratoon rice test protocol (CK) was repeated 3 times and the average value was taken.

The ratoon season of the test was after August 1, and the natural day length was shorter than the critical day length of Lingliangyou 472. Therefore, it was a conventional ratoon rice test.

Main Crop

Sowing date: February 26. Location: Nanning, Guangxi. Transplanting date: April 5.

Healing beginning date: June 12. Yellow ripening date: July 31. Whole growth period: 154 days.

Ratoon Crop (High Stubble)

Healing beginning date: August 28. Yellow ripening date: October 10. Whole growth period: 71 days.

The double-season late rice test protocol (CK) was repeated 3 times and the average value was taken.

Sowing date: July 16. Location: Nanning, Guangxi. Transplanting date: August 8.

Healing beginning date: October 2. Yellow ripening date: November 7. Whole reproductive phase: 114 days.

The cultivation techniques of conventional ratoon rice and double-season late rice are known to those skilled in the art, and relevant materials can also be referred to. The cultivation process of ratoon rice to which the invention applied will be described in detail below.

The critical day length of Lingliangyou 472 is about 13 hours and 10 minutes, and the day length in Nanning from May 11 to July 31 is greater than the critical day length of Lingliangyou 472. Under the premise of using only natural illumination and no shading, main crop of Lingliangyou 472 must complete photoperiod induction before May 11. In order to make the ratoon season be able to be treated under long day conditions for more than 30 days, main crop need to be harvested before June 30.

In 2018, on February 1, seedings were bred in Wanning, Hainan, and transplanted to the experimental field in Nanning on February 26. 30 holes were made per square meter, with 2 grain seedlings per hole. The base fertilizer shall be enough, and additional fertilizer shall be applied early. The strict control of nitrogen shall be performed in the later stage. For medium fertility soil, 40 kg of 25% rice special compound fertilizer per mu was applied as base fertilizer. 7 days after transplanting, the herbicide was applied in combination, followed by 7.5 kg of urea per mu. 7 kg of potassium chloride per mu was applied at the beginning of young ears differentiation. During the tillering stage, the dry and wet separation promoted tillering. When the total number of seedlings per mu reached 250,000 seedlings, drained off water timely to make the field dry in the sun. During the booting stage, it shall be wet mainly. During the heading stage, the thin-water layer shall be maintained. During the grouting stage, it shall be wet mainly humid mainly. It must be avoided by all means to drain water off too early. Pay attention to the prevention and control of pests and diseases in time, such as rice blast, bacterial blight, striped rice borer, rice leaf roller, sheath blight and rice planthopper. Harvested when 90% of grains matured, and maintained the health of ratoon stubbles and the strong vitality of ratoon buds. Left low stubbles of ratoon rice to which the invention applied and the high stubbles of conventional ratoon rice. Kept the soil moist but no water layer can be seen within 10 days after harvest. On the 11th day, shallow water was applied, and 30 kg of 25% rice special compound fertilizer and 7.5 kg of urea per mu were applied. In the later stage, the dry and wet separation promoted tillering. When the total number of seedlings per mu reached 250,000 seedlings, drained off water timely to make the field dry in the sun and control the seedlings. At the beginning of August, 5 kg of potassium chloride per mu was applied at the beginning of young ears differentiation. The whole growth period of ratoon rice to which the key technologies of the invention applied was about 108 days (see Table 4). Ratoon rice had good maturation uniformity and the highest yield, with the yield greatly increased comparing with the conventional ratoon rice and exceeded the double-season late rice yield level of Lingliangyou 472.

TABLE 4

The growth period and yield of Lingliangyou 472 in ratoon season

| type | Duration of harvest (day) | whole growth period (day) | number of grains per panicle | yield/kg |
|---|---|---|---|---|
| ratoon rice of the present invention | 63B | 108B | 147.6B | 528.2B |
| conventional ratoon rice ck | 28A | 71A | 100A | 300A |
| double-season late rice ck | 78B | 114B | 143.8B | 500.2B |

Note:
Different letters in the same column indicate that the difference is extremely significant ($P < 0.01$).

The yield of rice comes from photosynthesis. Conventional ratoon rice directly enters the stage of vegetative growth and reproductive growth in parallel. The whole growth period was only 60-80 days, and the products accumulated by photosynthesis are limited.

In the examples, the yield of ratoon rice to which the invention applied was higher than that of the double-season late rice, while the growth period of double-season late rice was longer than the growth period of ratoon rice, and both seemed to be contradictory. In fact, that was not the case. The rice stubble of ratoon rice has a certain nutrient storage, so generally, it can directly germinate 3 to 5 ratoon buds within 3 to 8 days. While for the double-season late rice, it took 20 to 30 days from sowing to transplanting into field having 3 to 5 basic seedlings, and it took 5 to 7 days to revive seedlings after transplanting. Therefore, ratoon rice can save 20 to 30 days compared to the double-season late rice. In this embodiment, the ratoon season of Lingliangyou 472 was about 108 days, corresponding to 128-138 days of double-season late rice, which exceeded the whole growth period of 114 days of Lingliangliang 472 as the double-season late rice, and thus the ratoon season had sufficient vegetative growth period. In the case of suitable conditions such as fertilizer, water, illumination and temperature conditions, it had a high yield potential.

The variety breeding method and cultivation method of ratoon rice provided by the invention are described in detail above. The principles and embodiments of the invention have been described with reference to specific examples, and the description of the above embodiments is only to assist in understanding the method of the invention and its core idea. It should be noted that those skilled in the art can make various modifications and changes to the invention without departing from the spirit and scope of the invention, these modifications and changes are also within the scope of the appended claims of the invention.

What is claimed is:

1. A method for rice ratooning, comprising selecting a photosensitive variety and cultivating under long-day conditions after harvesting a main crop of rice; wherein the photosensitive variety refers to a variety that long day may delay or prevent its photoperiod induction and thereby prolonging growth period; wherein the long day refers to an illumination time per day longer than critical day length of the photosensitive variety; wherein,
   a. in the equatorial region or the vicinity of the equator, the method comprises selecting a photosensitive variety with a critical day length shorter than 12 hours and 6 minutes, applying shading treatment for 8 to 30 days and giving 9-10 hours of natural illumination every day for completion of photoperiod induction, harvesting a main crop of rice, cultivating under long-day conditions, leaving low stubbles while maintaining a no-water layer or a thin-water layer with a water depth of no more than 3 cm within 7 days of the harvest of the main rice, applying fertilizer in the ratoon season to promote ratoon shoots with large number of tillers, and harvesting the ratoon rice;
   b. in the tropics, the method comprises selecting a photosensitive variety with a critical day length between 12 hours and 39 minutes and 13 hours and 10 minutes, completing photoperiod induction, harvesting a main crop of rice, cultivating under long-day conditions, leaving low stubbles while maintaining a no-water layer or a thin-water layer with a water depth of no more than 3 cm within 7 days of the harvest of the main rice, applying fertilizer in the ratoon season to promote ratoon shoots with large number of tillers, and harvesting the ratoon rice; and
   c. in the subtropics, the method comprises selecting a photosensitive variety with a critical day length between 12 hours and 47 minutes to 13 hours and 20 minutes, completing photoperiod induction, harvesting a main crop of rice, cultivating under long-day conditions, leaving low stubbles while maintaining a no-water layer or a thin-water layer with a water depth of no more than 3 cm within 7 days of the harvest of the main rice, applying fertilizer in the ratoon season to promote ratoon shoots with large number of tillers, and harvesting the ratoon rice.

2. The method as claimed in claim 1, wherein the photosensitive variety is selected and cultivated under continuous long-day conditions immediately after the completion of photoperiod induction of the main crop of rice.

3. The method as claimed in claim 1, further comprising selecting a low-node ratoon variety and/or performing low stubble treatment to promote germination and tillering of low-node buds, wherein the low-node buds refer to ratoon buds of the last 4th node and lower nodes.

4. The method as claimed in claim 1, wherein the duration of the long-day is for not less than 20 days.

5. The method as claimed in claim 1, wherein the long-day condition is provided by way of natural illumination or artificial illumination, and the artificial illumination may be switched to natural illumination without interval, or the artificial illumination may interrupt continuous dark cycle; the length and/or intensity of the long illumination prevents or delays photoperiod induction of ratoon shoots and tillers thereof.

6. The method as claimed in claim 1, wherein the photosensitive variety is a low-node ratoon variety and suitable to low stubble treatment; and the low-node ratoon variety refers to a variety that the low-node ratoon buds account for more than 30% of ratoon buds from all-nodes in the case of high stubble treatment, and the low stubble treatment refers to retaining low-node buds only, with the stubble height of 8-15 cm.

7. The method as claimed in claim 1, wherein after the completion of long-day, accumulative fertilization amount applied accounts for 70% to 90% of the total fertilization amount in the whole growth period of the ratoon rice after harvesting the main crop.

8. The method as claimed in claim 6, wherein specific water management of the low stubble treatment is: under a precondition of water content in soil greater than 60%, maintaining a no-water layer or a thin-water layer with a water depth of no more than 3 cm within 7 days of the harvest of the main rice.

* * * * *